(12) United States Patent
Perkins et al.

(10) Patent No.: US 12,415,093 B2
(45) Date of Patent: Sep. 16, 2025

(54) RADIOTHERAPY APPARATUS

(71) Applicant: Elekta Limited, Crawley (GB)

(72) Inventors: Clifford William Perkins, Crawley (GB); Trevor Burke, Crawley (GB); Rejean Leblanc, Crawley (GB); Ruud Verhaegh, Crawley (GB)

(73) Assignee: Elekta Limited, Crawley (GB)

( * ) Notice: Subject to any disclaimer, the term of this patent is extended or adjusted under 35 U.S.C. 154(b) by 293 days.

(21) Appl. No.: 18/061,258

(22) Filed: Dec. 2, 2022

(65) Prior Publication Data

US 2024/0181276 A1 Jun. 6, 2024

(30) Foreign Application Priority Data

Dec. 6, 2021 (GB) ...................................... 2117574

(51) Int. Cl.
*A61N 5/10* (2006.01)

(52) U.S. Cl.
CPC ......... *A61N 5/1081* (2013.01); *A61N 5/1048* (2013.01)

(58) Field of Classification Search
CPC ...... A61N 5/1048; A61N 5/1081; A61N 5/01; A61N 5/10; A61N 5/1001; A61N 5/1064; A61N 5/1065; A61N 2005/1022; A61N 2005/1092; A61N 5/1077; A61N 5/1082; A61N 2005/1057; A61N 2005/005; A61N 5/1084; A61N 2005/1095; A61N 5/1049; A61N 2005/1061; A61N 5/1042; A61N 5/1075; A47B 91/02; A61B 6/4447; A61B 6/4488; A61B 6/032; A61B 6/4435; G01N 3/04

USPC ................................................ 378/4, 15, 196
See application file for complete search history.

(56) References Cited

U.S. PATENT DOCUMENTS

| 6,823,037 B2 * | 11/2004 | Riemer | G01N 23/046 378/197 |
| 6,840,673 B2 * | 1/2005 | Moritake | A61B 6/035 378/198 |
| 6,959,068 B1 * | 10/2005 | Sommer | A61B 6/04 378/208 |

(Continued)

FOREIGN PATENT DOCUMENTS

| EP | 1738798 | 1/2007 |
| EP | 2865417 | 4/2015 |
| GB | 2519592 A | 4/2015 |

OTHER PUBLICATIONS

"European Application Serial No. 22211204.7, European Search Report dated May 9, 2023", (May 9, 2023), 7 pgs.

(Continued)

*Primary Examiner* — Irakli Kiknadze
(74) *Attorney, Agent, or Firm* — Schwegman Lundberg & Woessner, P.A.

(57) ABSTRACT

Disclosed herein is a radiotherapy apparatus comprising a gantry rotatable about a gantry rotation axis, and a plurality of rotatable rollers positioned underneath the gantry and configured to support the gantry. A first rotatable roller of the plurality of rotatable rollers is configured to rotate about a first axle, and the first axle is configured to rotate about a first axle rotation axis. The first axle is configured such that rotation of the first axle about the first axle rotation axis displaces the first rotatable roller in a direction substantially perpendicular to the gantry rotation axis.

18 Claims, 9 Drawing Sheets

(56) References Cited

U.S. PATENT DOCUMENTS

2004/0062343 A1* 4/2004 Brunnett ............... A61B 6/035
378/4
2009/0139344 A1 6/2009 Lindeman

OTHER PUBLICATIONS

"British Application No. 2117574.0, Office Action dated May 27, 2022", (May 27, 2022), 5 pgs.

* cited by examiner

RADIOTHERAPY APPARATUS

CLAIM FOR PRIORITY

This application claims the benefit of priority of United Kingdom Application No. 2117574.0, filed Dec. 6, 2022, which is hereby incorporated by reference in its entirety.

This disclosure relates to a radiotherapy apparatus and method, and in particular to an apparatus comprising components and/or means for mitigating or eliminating the 'corkscrew' effect.

BACKGROUND

Radiotherapy can be described as the use of ionizing radiation, such as X-rays, to treat a human or animal body. Radiotherapy is commonly used to treat tumors within the body of a patient or subject. In such treatments, ionizing radiation is used to irradiate, and thus destroy or damage, cells which form part of the tumor.

For the purposes of radiotherapy treatment, it is desirable to deliver a particular dose to a target region while minimizing the dose to surrounding areas of healthy tissue. Thus, the accuracy of the delivery of the treatment beam is of the utmost importance during radiotherapy treatment. Any inaccuracy in delivery of the treatment beam can negatively impact treatment efficacy, and may result in a higher dose being delivered to healthy tissue.

A radiotherapy device can comprise a gantry which supports a beam generation system, or other source of radiation, which is rotatable around a patient. For example, for a linear accelerator (linac) device, the beam generation system may comprise a source of radio frequency energy, a source of electrons, an accelerating waveguide, beam shaping apparatus, etc.

The gantry of a radiotherapy device may be provided as a rotatable drum with a circular cross-section. The gantry is rotatable about a gantry rotation axis. The beam generation system is coupled to the rotatable gantry, and therefore rotation of the gantry allows for the beam of therapeutic radiation to be applied from multiple angles around the patient during a treatment session. Radiation is deliverable toward a radiation isocenter, which may be positioned on the gantry rotation axis regardless of the angle to which the radiation source is rotated around the gantry. The gantry drum may be supported by a number of rollers, such as wheels. Devices such as rollers, and the like, can be present to support or drive the rotation of the gantry drum.

SUMMARY

It has been found that, due to forces generated during its rotation, a rotating gantry drum can be caused to translate along its axis of rotation. The gantry drum may become displaced in one direction along the rotational axis when the drum undergoes a rotation in a first direction, and the drum may return along substantially the same axial path when rotated in the opposite direction. This movement can be of the order of 1 mm or more. This translation of the gantry drum can be referred to as 'corkscrewing', and can be referred to as the 'corkscrew' effect.

Any movement of the gantry along its axis causes a shift in isocenter location, and thus affects the accuracy of treatment beam delivery. The forces generated by this 'corkscrewing' of the gantry drum can also bend or damage brackets holding rollers used to rotate the gantry in a radiotherapy apparatus.

Roller bearings can be used to attempt to mitigate the corkscrew effect, however, these roller bearings have a limited effect due to the large forces generated by the 'corkscrewing' and the significant mass of the gantry. These large forces generated by the corkscrewing can lead to damage of the components of the radiotherapy device.

According to an aspect of the present disclosure, there is provided a radiotherapy apparatus comprising a gantry rotatable about a gantry rotation axis, and a plurality of rotatable rollers positioned underneath the gantry and configured to support the gantry. A first rotatable roller of the plurality of rotatable rollers is configured to rotate about a first axle, and the first axle is configured to rotate about a first axle rotation axis. The first axle is configured such that rotation of the first axle about the first axle rotation axis displaces the first rotatable roller in a direction substantially perpendicular to the gantry rotation axis.

Optionally, the apparatus further comprises a support structure comprising a first axle holder configured to support the first axle and thereby define the first axle rotation axis.

Optionally, the first axle comprises different sections along its length, including an eccentric section, and the first roller is configured to rotate about the eccentric section.

Optionally, the eccentric section is positioned eccentrically with respect to the first axle rotation axis.

Optionally, the eccentric section is offset with respect to the first axle rotation axis.

Optionally, the eccentric section has a central axis which is parallel with, but which does not align with, the first axle rotation axis.

Optionally, the eccentric section defines a first roller rotation axis about which the first rotatable roller rotates, wherein the first roller rotation axis is displaced from the first axle rotation axis.

Optionally, the first axle is configured such that, by rotating the first axle about the first axle rotation axis in a first rotational direction, the first roller rotation axis is rotated in the first rotational direction.

Optionally, the first axle further comprises holding sections positioned either side of the eccentric section, wherein the holding sections pass through the axle holder.

Optionally, the holding sections are substantially cylindrical, and have a shared central axis which aligns with the first axle rotation axis.

Optionally, the plurality of rotatable rollers comprises at least one drive roller configured to drive rotation of the gantry.

Optionally, the plurality of rotatable rollers further comprises a second rotatable roller, wherein the second rotatable roller is configured to rotate about a second roller axle, wherein the second axle is configured to rotate about a second axle rotation axis, and wherein the second axle is configured such that rotation of the second axle about the second axle rotation axis displaces the second rotatable roller in a direction substantially perpendicular to the gantry rotation axis.

Optionally, the first and second axles are horizontally displaced with respect to each other along an axis substantially perpendicular to the gantry rotation axis.

Optionally, the first and second rotatable rollers are positioned either toward the rear, or toward the front, of the gantry.

According to another aspect of the present disclosure, there is provided a method for displacing a first roller of a plurality of rotatable rollers positioned underneath a gantry of a radiotherapy device. The rotatable rollers are configured to support the gantry, and the gantry is rotatable about a gantry rotation axis. The first rotatable roller of the plurality of rotatable rollers is configured to rotate about a first axle, and the first axle is configured to rotate about a first axle rotation axis. The first axle is configured such that rotation of the first axle about the first axle rotation axis displaces the first rotatable roller in a direction substantially perpendicular to the gantry rotation axis. The method comprises rotating the first axle about its rotation axis to displace the first rotatable roller in the direction substantially perpendicular to the gantry rotation axis.

The radiotherapy device for use with the method may be in accordance with one or more of the radiotherapy devices disclosed herein.

BRIEF DESCRIPTION OF THE DRAWINGS

In the drawings, which are not necessarily drawn to scale, like numerals may describe similar components in different views. Like numerals having different letter suffixes may represent different instances of similar components. The drawings illustrate generally, by way of example, but not by way of limitation, various embodiments discussed in the present document.

DETAILED DESCRIPTION

In overview, and without limitation, the present disclosure relates to radiotherapy apparatus comprising components and/or means for mitigating, or else eliminating, an undesirable corkscrewing effect. The gantry is supported by a plurality of rollers (e.g. wheels), which are in turn supported by an under-gantry support structure. At least one of the rollers can be displaced in a direction substantially perpendicular to the gantry rotation axis. Hence, the gantry's position on the supporting rollers, and the gantry's alignment with the rotational axes of the rollers, can be adjusted. By making this kind of adjustment, it is possible to mitigate the corkscrewing effect, or else find a 'sweet spot' in which the corkscrewing effect may be eliminated entirely. Accordingly, the radiotherapy device stability is improved, and in particular the device's axial stability during rotation of the device can be improved.

An individual roller can be adjusted by virtue of an axle comprising an eccentric section, where the roller is positioned and configured to rotate around (and with respect to) the eccentric section. The axle and eccentric section are configured such that rotation of the axle about its own rotational axis causes a displacement of the roller in a direction substantially perpendicular to the gantry rotation axis. Also disclosed herein is a method for displacing one or more rollers in a manner which mitigates or eliminates the corkscrewing effect.

Figure 1:
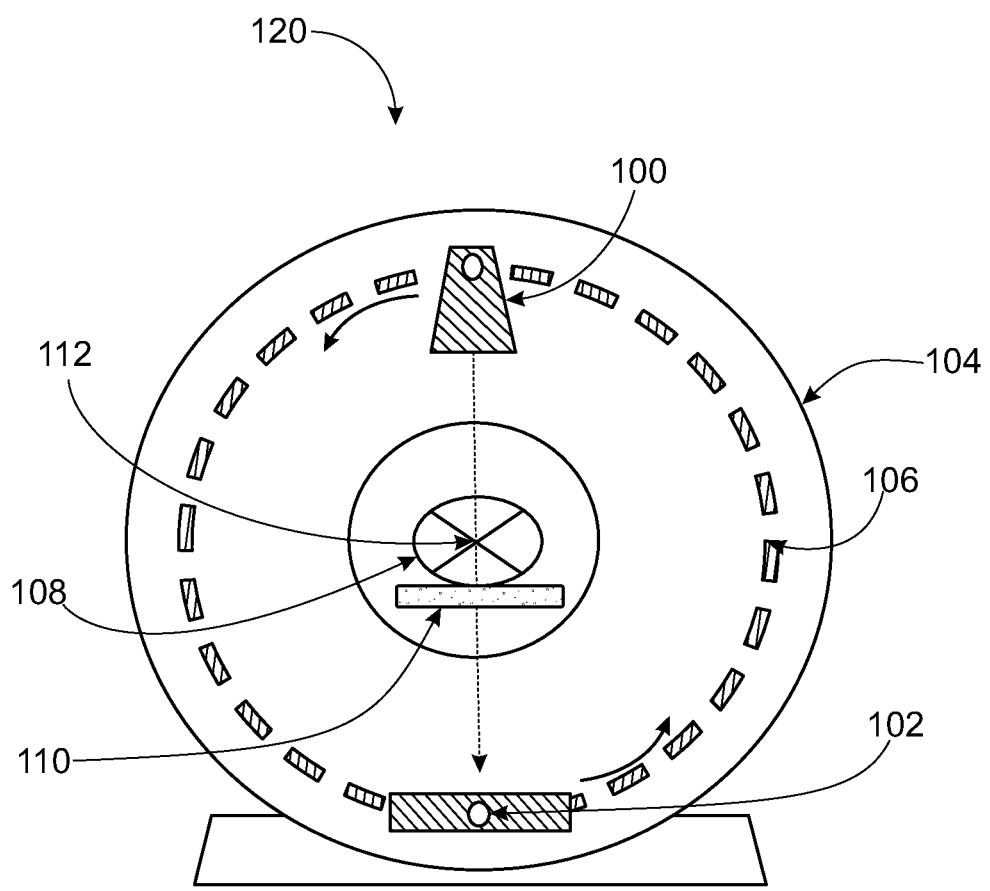
FIG. 1 depicts a radiotherapy apparatus according to the present disclosure.

FIG. 1 depicts a radiotherapy apparatus according to the present disclosure. The arrangement described should be considered as providing one or more examples of a radiotherapy apparatus 120 and it will be understood that other arrangements are possible. FIG. 1 shows a cross-section through a radiotherapy apparatus 120 comprising a radiation source 100 and a detector 102 attached to a gantry 104. The gantry 104 may take the form of a substantially cylindrical drum. The radiation source 100 and the detector 102 are fixed to the gantry drum 104 so as to rotate with the gantry drum 104. The radiation source 100 and the detector 102 are arranged diametrically opposite one another.

FIG. 1 also depicts a subject 108 on a support surface 110. The support surface 110 may be moved longitudinally relative to the gantry drum 104 (i.e. away from the plane of the gantry drum 104), for example to aid positioning of the subject 108. In some examples, the support surface 110 may be moved along other translational axes (e.g. in the plane of the gantry) and/or rotational axes. A controller may have access to position and/or movement information for the support surface 110, and may be configured to position a patient according to the requirements of a particular radiotherapy treatment plan. As radiation is applied to the subject 108, for example according to a treatment plan, the radiation source 100 and the detector 102 rotate together with the gantry 104 such that they are always arranged 180° from one another. The radiation source 100 directs radiation towards the subject 108 from various angles around the subject 108 in order to spread out the radiation dose received by healthy tissue to a larger region of healthy tissue while building up a prescribed dose of radiation at a target region. As shown in FIG. 1, radiation may be emitted in a plane which is perpendicular to the axis of rotation of the radiation source 100. Thus, radiation may be applied to a radiation isocentre 112 at the centre of the gantry drum 104 regardless of the angle to which the radiation source 100 is rotated around the gantry drum 104. The radiation can be shaped or limited using a collimator, for example a multi-leaf collimator, arranged in the path of a radiation beam.

Figure 2B:
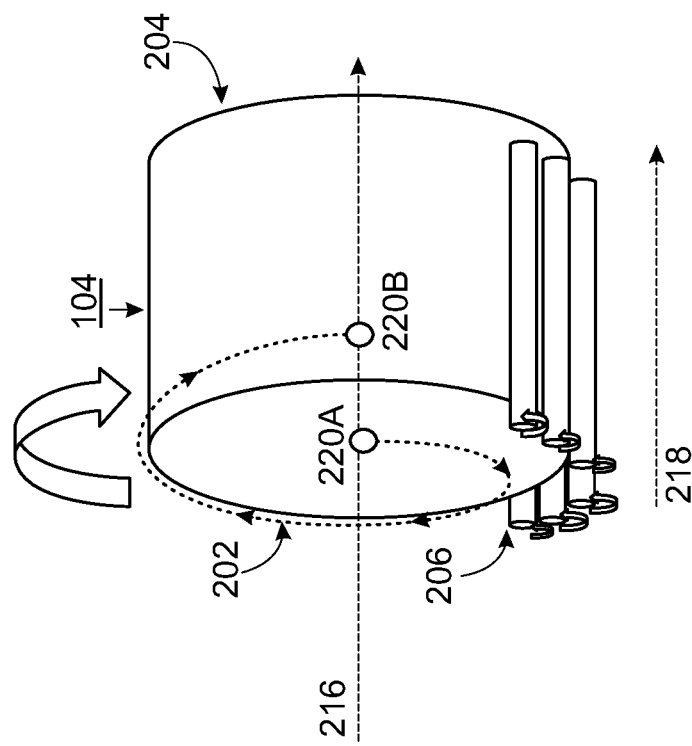
FIG. 2a and FIG. 2b depict a gantry drum arrangement experiencing a corkscrew effect.
Figure 2A:
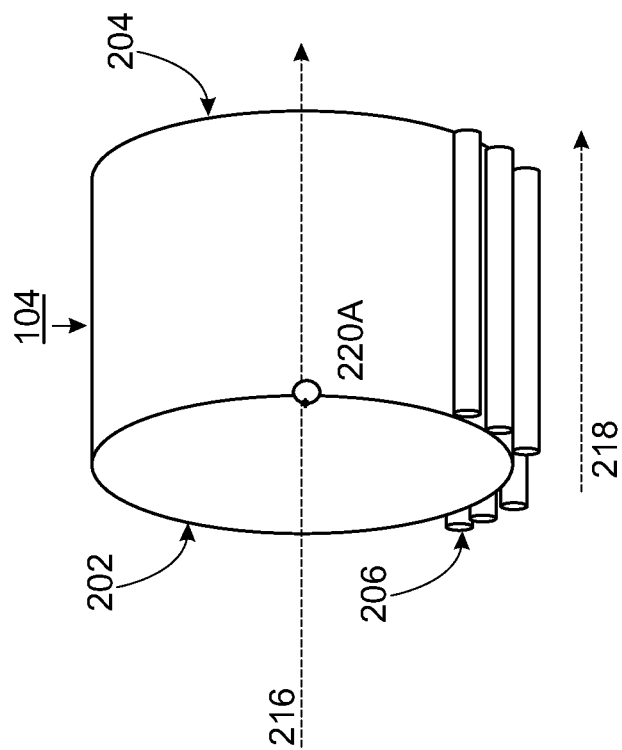

FIG. 2A is a simplified schematic diagram of a gantry. The gantry is a drum-shaped gantry as described above in relation to FIG. 1. Such a gantry may form part of the radiotherapy apparatus 120 described with respect to FIG. 1, though a number of components described in relation to FIG. 1 are not shown here for simplicity. The gantry itself may comprise additional components, such as an arm for connecting to a source of radiation. However, FIGS. 2A and 2B primarily depict the drum 104 of the gantry. The drum 104 has a circular cross section, and is substantially cylindrical in shape. The drum 104 is oriented in the vertical plane, i.e. the central axis of the drum 104 is substantially parallel with a horizontal axis and substantially perpendicular to a vertical axis. The drum 104 comprises a first end 202, and a second end 204, each comprising a circular cross-section. The first end 202 may be proximal to the subject 108 during treatment, and the radiation source 100 and the detector 102 may be fixed or coupled to the first end 202 of the gantry drum 104, for example via an arm. The radiation source 100 and detector 102 rotate with the gantry drum 104 during treatment. The first end may also be referred to as the 'front' or 'T' end of the gantry. The second end 204 may be distal to the subject 108 during treatment, and may be connected to, for example, a power supply, a cooling system, and/or other components of the radiotherapy apparatus. The second end may also be referred to as the 'rear' or 'G' end of the gantry.

A number of rollers 206 support the drum 104 as it rotates. The rollers 206 may be substantially cylindrical as shown, and may run longitudinally along the underside of the drum. The rollers 206 substantially align along a roller axis 218, which is substantially parallel to the gantry rotational axis 216. One or more of the rollers are drive rollers. During use, the drive rollers are driven in order to cause the gantry drum 104. Each roller 206 is rotatable around a parallel roller rotational axis unique to each roller 206.

FIG. 2B depicts the gantry drum during or directly after a rotation of the drum 104 has occurred. Numerous forces act upon the drum 104 during its rotation. Such forces include rotational forces imparted by the drive rollers, forces due to the effect of gravity on the drum 104, frictional forces between rollers 206 and the rotating gantry drum 104, and the like. These forces do not act on the gantry 104 in a uniform manner, and may introduce an imbalance of forces. For example, gravitational forces act on the outer surfaces of the drum 104 to mechanically deform them, and because heavy components are attached to the gantry at different parts around its circumference, this deformation is variable depending on the angle of gantry rotation.

An imbalance of forces, mechanical tolerances, motion, and mechanical deformations caused by gravity can all contribute to introducing an angle between the gantry rotational axis 216 and the roller axis 218, which may in turn cause the drum 104 to 'steer' in one direction or another. For example, the drum 104 may move longitudinally along its rotational axis, as depicted in FIG. 2B. In FIG. 2B, the drum 104 is displaced in a direction parallel to arrow 217. In other implementations, the drum 104 may be displaced in the opposition direction to arrow 217. The direction of this longitudinal displacement may depend on the direction of rotation of the gantry drum. For example, a gantry drum may rotate in a clockwise direction and become displaced in a first direction, and may rotate in an anti-clockwise direction and become displaced in a second direction, opposite to the first direction. This is known as the 'corkscrewing' of the gantry, or the 'corkscrew' effect, due to the similarity between the rotational displacement of the gantry and the movement caused by the twisting of a corkscrew.

The 'corkscrew'-like motion of the gantry can be observed by following a point 220A on the surface of the gantry drum. The point is defined relative to the gantry rotational axis 216 in the longitudinal direction. As the drum rotates, the point 220A is displaced, from its initial position, longitudinally along the gantry rotational axis 216. As depicted by the trajectory 222 on FIG. 2B, the point 220A follows a helical path as the drum 104 rotates. At some later time, the point on the drum is no longer at location 220A defined relative to the gantry rotational axis 216, but is at location 220B. This displacement is merely shown to illustrate the displacement of the gantry, and is not to scale.

Because the gantry is configured to support the radiation source 100 and detector 102, any displacement of the gantry due to the corkscrewing effect will result in a displacement of the radiation source 100 and the detector 102. Such a displacement of the radiation source 100 can cause small shifts in isocenter 112 location, and thus affect the efficacy and accuracy of treatment beam delivery. A displacement of the gantry drum 104 in the manner of FIG. 2B may reduce the efficacy of treatment by reducing the accuracy with which the therapeutic treatment beam is applied.

FIGS. 3a-d depicts a radiotherapy apparatus 500. The apparatus 500 comprises a gantry 504 in the form of a drum. The gantry 504 comprises an axis of rotation 516.

Figure 3A:
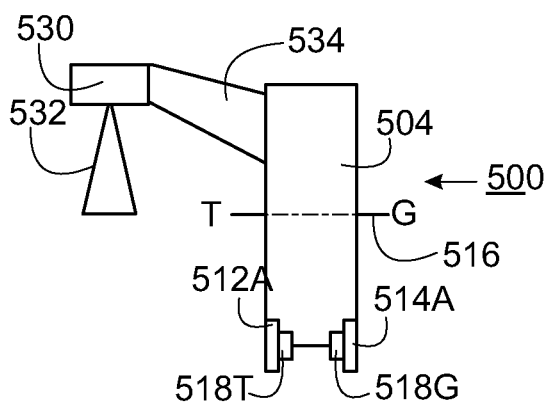
FIGS. 3a-d depict a radiotherapy apparatus.

The apparatus 500 comprises a source of radiation 530 which is coupled to the gantry via an arm 534. FIG. 3a schematically depicts a beam of radiation 532 being emitted from the source of radiation 530. The source of radiation 530 is part of a beam generation system which comprises an electron gun, a waveguide to accelerate electrons emitted by the electron gun toward a target, and a target which, when struck by high energy electrons, produces high energy X-rays.

Figure 3B:
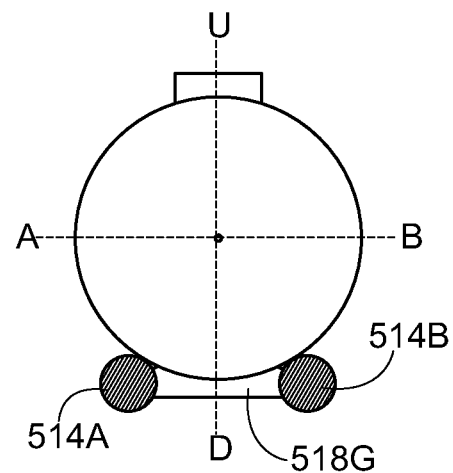

The gantry rotation axis 516 lies along a T-G axis, where the G refers to the (electron) gun end of the waveguide and the T refers to the target end of the waveguide in an implementation in which the waveguide is comprised within the arm 534. The use of this terminology for the T-G axis is merely used to describe the geometry of the radiotherapy apparatus 500, and does not imply that the waveguide need be oriented in this way in implementations of the present invention. The T-G axis passes through the isocenter and is horizontal when the apparatus is viewed from the view depicted in FIG. 3a. The 'front' of the device 500, i.e. the side on which the source of radiation 530 is positioned, can be described as the T end of the device 500. Similarly, the rear of the device 500 can be described as the G end of the device 500. The geometry of the device 500 can be further described with respect to an A-B axis, which is depicted in FIG. 3b. The A-B passes through the isocenter, is orthogonal with the T-G axis, and is horizontal when the apparatus is viewed from the view depicted in FIG. 3b. Finally, the apparatus can be described with respect to a U-D (up-down) axis. The U-D axis also passes through the isocenter and is orthogonal with the T-G and A-B axes. Where appropriate for improving clarity of description, certain components herein may be referred to using these axes, and certain reference numerals herein are appended with letters G, T, A, B, U, D, particularly where the component is part of a plurality of similar components and it is useful to distinguish between the components by reference to the apparatus geometry.

The gantry 504 is supported on a plurality of rotatable rollers 512A,B and 514 A,B. The rollers are substantially cylindrical, and may take the form of wheels or elongated cylinders. Herein, the term "rollers" will be used to describe rotatable cylinders on which the gantry is supported, and the term rollers should be understood to describe wheel-shaped rollers (as shown in FIGS. 3a-d) and also cylinders with a longer central axis than might be typically associated with a "wheel" shape.

Each of the rollers 512A,B and 514 A,B is positioned underneath the gantry 504 and is configured to support the gantry 504. The rollers 512A,B and 514 A,B are each in contact with the gantry 504. The outer circumferences of the rollers 512A,B and 514 A,B are in contact with an outer circumference of the gantry 504. The rollers 512A,B and 514 A,B are rotationally coupled with the gantry 504 such that the rollers 512A,B and 514 A,B and the gantry 504 rotate together about their respective rotational axes.

One or more of the plurality of rollers 512A,B and 514 A,B may be a drive roller. In some implementations, all of the rollers 512A,B and 514 A,B are drive rollers. The one or more drive rollers are coupled with a motor or other drive means. The one or more drive rollers enable rotation of the gantry 504 by actuation of the motor or other drive means. To rotate the gantry, the motor(s) or other drive means control rotation of the drive rollers, which via friction causes the gantry 504 to rotate. As each of the rollers 512A,B and 514 A,B is rotationally coupled with the gantry 504, each of the rollers rotates with the gantry 504 regardless of whether or not it is a drive roller.

In the implementation shown in FIGS. 3a-d, there are four rotatable rollers configured and positioned to support the gantry 104, however there may be more, or fewer. In the implementation shown, the four rollers comprise a plurality of 'front' drive wheels 512A,B. These front wheels are at the T end of the gantry 504. The plurality of drive wheels further comprises a plurality of 'rear' drive wheels 514A,B. These rear wheels 514A,B are at the G end of the gantry 504. In other words, FIGS. 3a-d depict an implementation in which there are four drive wheels total, with two front drive wheels 512a,b and two rear drive wheels 514a,b. By positioning two rollers toward the front end of the gantry and two rollers toward the rear end of the gantry, the gantry is well-supported. As will be described elsewhere herein, at least one of the rollers is adjustable in order to mitigate or prevent a corkscrew effect, and having four rollers positioned as shown allows one or more of the rollers to be adjusted while ensuring the gantry 104 remains stable throughout the adjustment.

The radiotherapy apparatus 500 also comprises at least one support structure. The support structure(s) supports the rotatable rollers and holds them in place as they rotate. In FIGS. 3a-d, two support structures are shown: a front support structure 518T toward the T end of the apparatus 500 which supports the front rollers 512A and 512B; and a rear support structure 518G toward the G end of the apparatus 500 which supports the rear rollers 514A and 514B. The support structures 518T,G may support the rollers via axles and axle holders (not shown in FIGS. 3a-d).

It will be appreciated that, by adjusting the position of one or more of the rollers 512A,B and 514A,B, it is possible to adjust the position of the gantry 504. In particular, it is possible to find a position of the rollers 512A,B and 514A,B in which a corkscrewing movement of the gantry 504 is mitigated, or else eliminated entirely. One can think of this as adjusting the relative positioning of the gantry's rotational axis with respect to the respective rotational axes of each of the rollers 512A,B and 514A,B until there is no resultant force which can cause a corkscrewing effect.

FIG. 3b depicts a rear view of a configuration of the radiotherapy apparatus 504 in which the front rollers 512A,B and the rear rollers 514A,B are aligned with one another. In other words, the rotational axes of the roller 512A and rear roller 514A are substantially parallel and aligned with one another, and the the rotational axes of the roller 512B and rear roller 514B are substantially parallel and aligned with one another. In a mathematically ideal mechanical system, there should be no corkscrewing effect as the gantry 504 rotates in this configuration. However, due to mechanical stresses caused by heavy arm 534 and radiation source 530, mechanical tolerances, motion and radial acceleration and deceleration, and other imperfections and deviations described elsewhere herein, a real apparatus in this configuration may still experience a corkscrewing effect as the gantry rotates on the rotatable support rollers 512A,B and 514A,B.

Figure 3C:
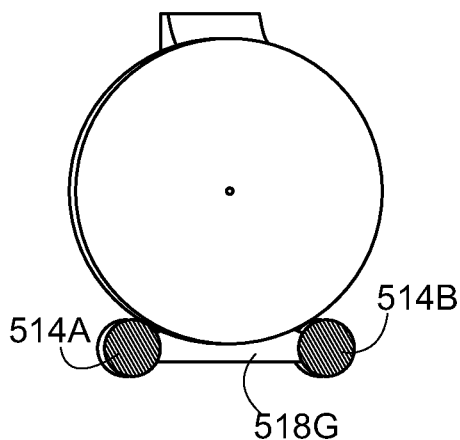
Figure 3D:
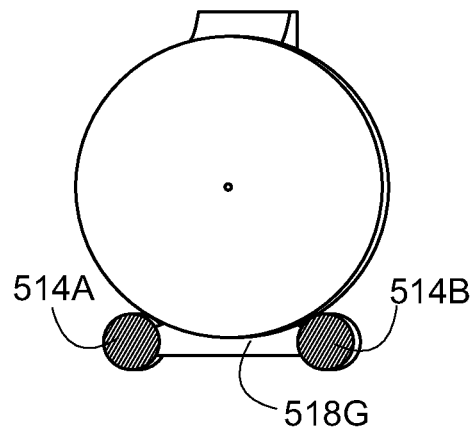

FIG. 3c depicts a rear view of a configuration of the radiotherapy apparatus 504 in which the rear wheels 514A, B, have both been shifted in the B direction. FIG. 3d depicts a rear view of a configuration of the radiotherapy apparatus 504 in which the rear wheels 514A,B have both been shifted in the A direction. By adjusting the position of the rear wheels in this way, it is possible to find a 'sweet spot' in which corkscrew motion is mitigated or else removed entirely. The sweet spot can be thought of as a position in which forces acting on the gantry along the G-T axis are eliminated, or reduced as much as possible.

Shifting the rear rollers 514A, B in this manner, and/or by similarly shifting the front wheels 512A,B, the position of the gantry rotation axis 516 in space may be adjusted. In particular, the gantry rotation axis 516 can be shifted with respect to the rotation axes of the rollers. By adjusting the relative position of the gantry rotation axis 516 with respect to the roller rotation axes, it is possible to find a "sweet spot" in which the cork-screwing effect is eliminated. In other words, by adjusting the relative positions of the rear wheels with respect to the front wheels, it is possible to find a configuration in which rotation of the gantry 504 does not result in the gantry 504 moving longitudinally along its rotation axis 516. In this way, the radiation source 530 does not move along the T-G axis as the gantry 504 is rotated, and the radiation isocenter tolerance of the apparatus 500 is improved.

Figure 4A:
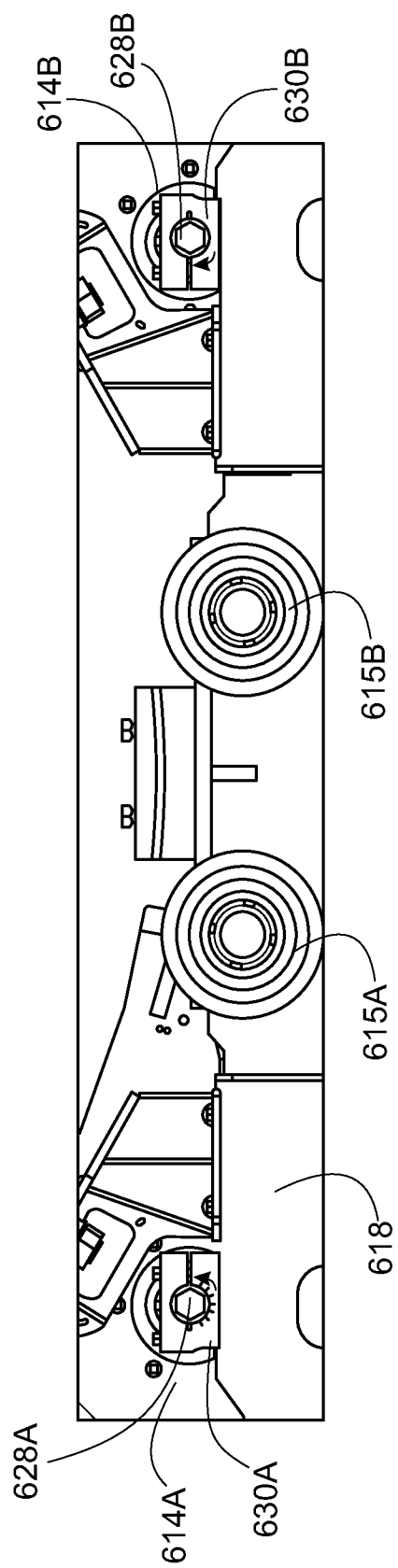
FIGS. 4a and 4b depict a support structure and a plurality of support rollers for supporting a gantry of a radiotherapy apparatus, such as the radiotherapy apparatus depicted in FIGS. 3a-d.
Figure 4B:
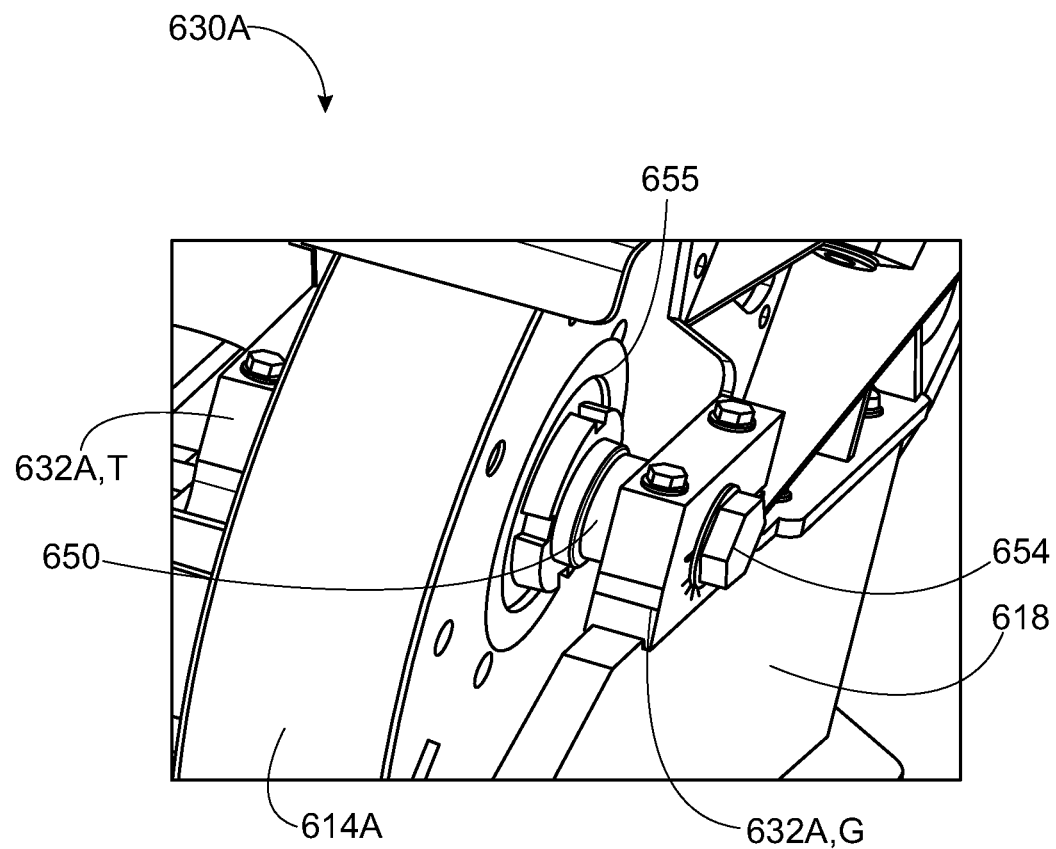

FIG. 4a and FIG. 4b depict a support structure 618 and a plurality of support rollers which are configured and positioned for supporting a gantry of a radiotherapy apparatus; for example, a radiotherapy apparatus as described above in relation to FIGS. 3a-d. FIG. 4a shows a rear view of the support structure 618, and shows the support rollers positioned at the rear of the apparatus. The support structure 618 comprises two axle holders 630A, 630B which are displaced from one another along the A-B axis. In other words, the axle holders 630A, 630B are horizontally displaced from one another in a direction substantially perpendicular to the gantry rotation axis. The axle holders 630A, 630B each hold (i.e. support) an axle, around which a rotatable roller rotates. With respect to FIG. 4a, axle holder 630A holds an axle about which roller 614A rotates, and axle holder 630B holds an axle about which roller 614B rotates.

The apparatus depicted in FIG. 4a also comprises two idler wheels 615A, 615B. These wheels 615A, 615B form part of the plurality of rollers positioned underneath the gantry. The idler wheels are optional, and are positioned and configured to contact the gantry and provide additional support as the gantry rotates. The gantry drum itself is not shown in FIGS. 4a,4b for increased clarity; however in use the drum of the gantry will contact each of the rotatable rollers.

FIG. 4b depicts the axle holder 630A in greater detail. The axle holder 630A comprises two axle holding elements 632. The axle holding elements 631A and 632A are positioned either side of a rotatable roller 614A. One axle holding element 632A, T is located on the T side of the roller and the other axle holding element is located on the G side of the roller 632A,G. The axle holding elements 631A, 632A each comprise an aperture through which the axle 650 may pass. The axle 650 may be referred to as a roller axle 650. The roller 614A and the axle 650 are configured such that the roller 614A may be rotated around, and with respect to, the axle 650. As such, the roller axle is a fixed axle, because, in use as the gantry rotates, the axle 650 does not rotate with the roller 614A. The apparatus further comprises a wheel bearing 655 which enables the roller 614A to rotate around the roller axle 650.

While the axle 650 may be described as a fixed axle because it does not rotate with the roller 614A as the gantry rotates, it may itself be rotated in order to adjust the position of the roller 614A. The axle 650 itself has a rotation axis, and is configured such that rotation of the axle about the axle rotation axis displaces the rotatable roller in a direction substantially perpendicular to the gantry rotation axis. The form and function of the axle 650 will be described in greater detail with respect to FIGS. 5 and 6.

Figure 5:
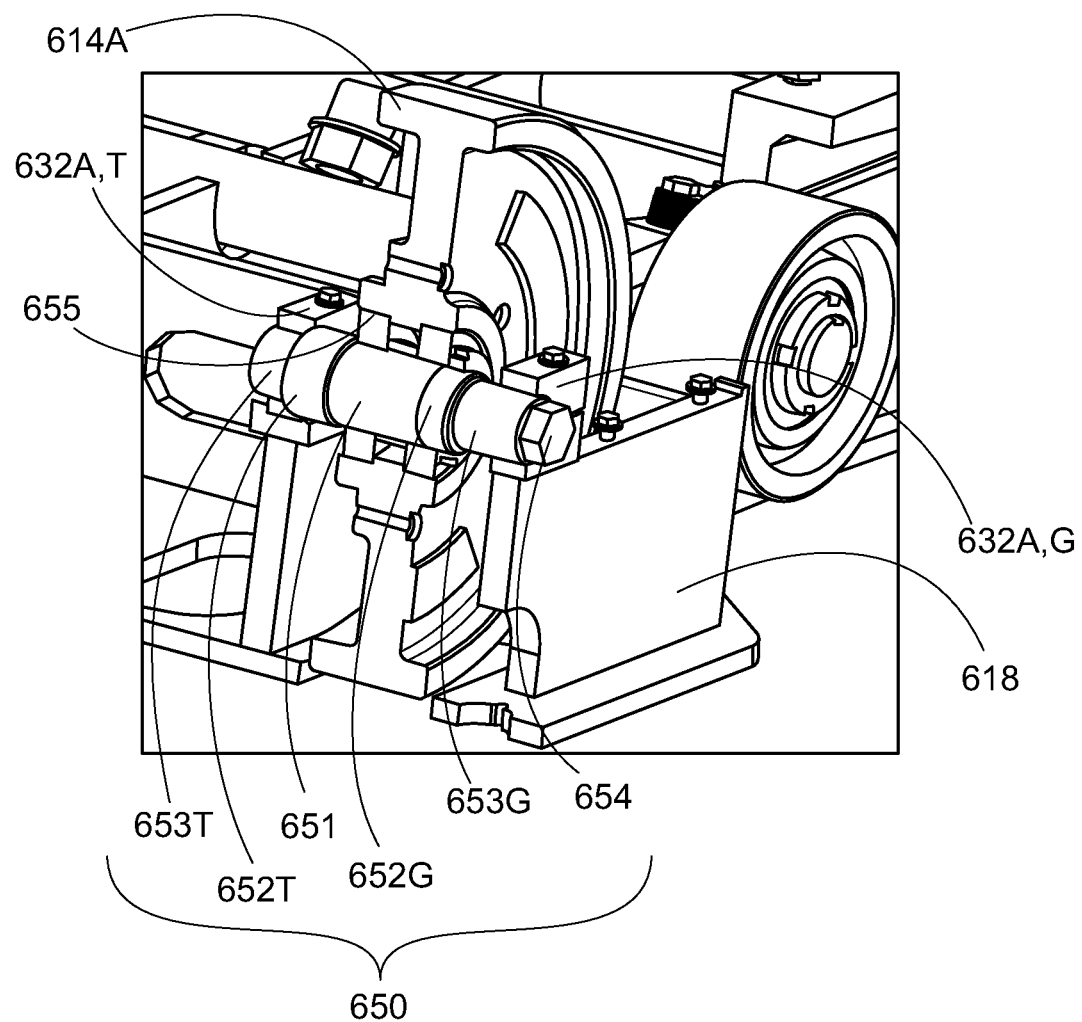
FIG. 5 depicts a cross-section through a rotatable roller and roller bearing of the apparatus depicted in FIGS. 4a and 4b

FIG. 5 depicts a cross-section through the rotatable roller 614A and roller bearing 660 depicted in FIGS. 4a and 4b in order to better depict roller axle 650. Roller axle 650 is not depicted in cross-section, in order to provide a better visual aid to understanding its form and function.

The roller axle 650 is comprised of different sections along its length. The sections are substantially circular in cross-section, and have different radii. The roller axle 650 comprises a first section 651 about which the first roller 614A rotates in use. The first section 651 may be referred to as an eccentric section, or an offset section. The first section is positioned eccentrically with respect to the first axle rotation axis. The first section 651 comprises a first radius. As can be appreciated from FIG. 5, the first section 651 is the part of the axle 650 which is in contact with and coupled with the roller bearing 660. The first section 651 and the roller bearing 660 share a common central axis, and this central axis defines the rotational axis of the roller 614A. The first section 651 may be described as an eccentric or an offset section, as the first section is positioned eccentrically (offset) with respect to the rotation axis of the axle 650. Accordingly, the rotational axis about which the roller 614A is rotated is also offset with respect to the rotational axis of the axle 650.

The roller axle 650 further comprises two sections having a second radius. These sections may be referred to as clamping sections. The clamping sections are optional. These clamping sections are positioned either side of the first section 651, with a first clamping section 652G being positioned toward the rear side of the apparatus compared with the other clamping section 652T. The second radius of the clamping sections 652T,G is larger than the first radius of the first section 651, such that sections 652T,G act to clamp the roller 614A and roller bearing 660 in place around the first section 651 of roller axle 651.

The roller axle 650 further comprises two sections having a third radius. These sections may be referred to as holding sections. These holding sections are positioned either side of the first section 651, with one section 653G being positioned toward the rear side of the apparatus compared with the other section 653T. In implementations where the apparatus comprises clamping sections 652G,T, the clamping sections 652G,T are positioned between the first section 651 and the respective holding section 653G,T. The third radius is less than the first and the second radii. Each holding section 653T,G passes through an aperture in an axle holding element 632. Each axle holding element 632 may be tightened or loosened, i.e. such that the aperture size can be increased or reduced. In ordinary use, the axle holding elements 632 are tightened to clamp the holding sections 653T tightly in place such that the axle 650 is a fixed, stationary axle.

As described above, the first section 651 of the axle 650 is the part of the axle about which the roller 614A is configured to rotate. The central axis of the first section 651 defines the rotational axis of the roller 614A. This first section 651 of the axle 650 is offset with respect to the central axis of the holding sections 653 of the axle 650. It is the holding sections 653 of the axle 650, and their interaction with the axle holder, which define the rotational axis of the axle 650. Accordingly, the rotational axis of the rotatable roller 614A is offset with respect to the rotational axis of the axle 650. Because the first section 651 is offset with respect to the axle rotation axis (as defined by the axle holder), the axle 650 is configured such that rotation of the axle 650 about the axle rotation axis displaces the rotatable roller 614A. The axle 650 and its rotation axis is substantially parallel with the gantry rotation axis, and therefore rotation of the axle 650 causes the rotatable roller 614A to be displaced in a direction substantially perpendicular to the gantry rotation axis.

Optionally, an axle cap 654 is provided at a distal end of the roller axle 650. Such an axle cap can be used to facilitate rotation of the roller axle 650 when the axle holding elements 632 are loosened. The axle cap may comprise, for example, a nut, a bolt, or both, and may be substantially hexagonal in shape (as shown in FIG. 5).

When the radiotherapy apparatus is installed on site, for example at a hospital, or else when the apparatus is undergoing maintenance, the axle holding elements 632 may be loosened and the axle 650 may be rotated about its rotational axis in order to adjust the position of the rotatable roller 614A. The axle 650 can be rotated via a rotation of the axle cap 654, for example via a wrench, spanner or a specialised tool configured to interact with the axle holder.

Figure 6:
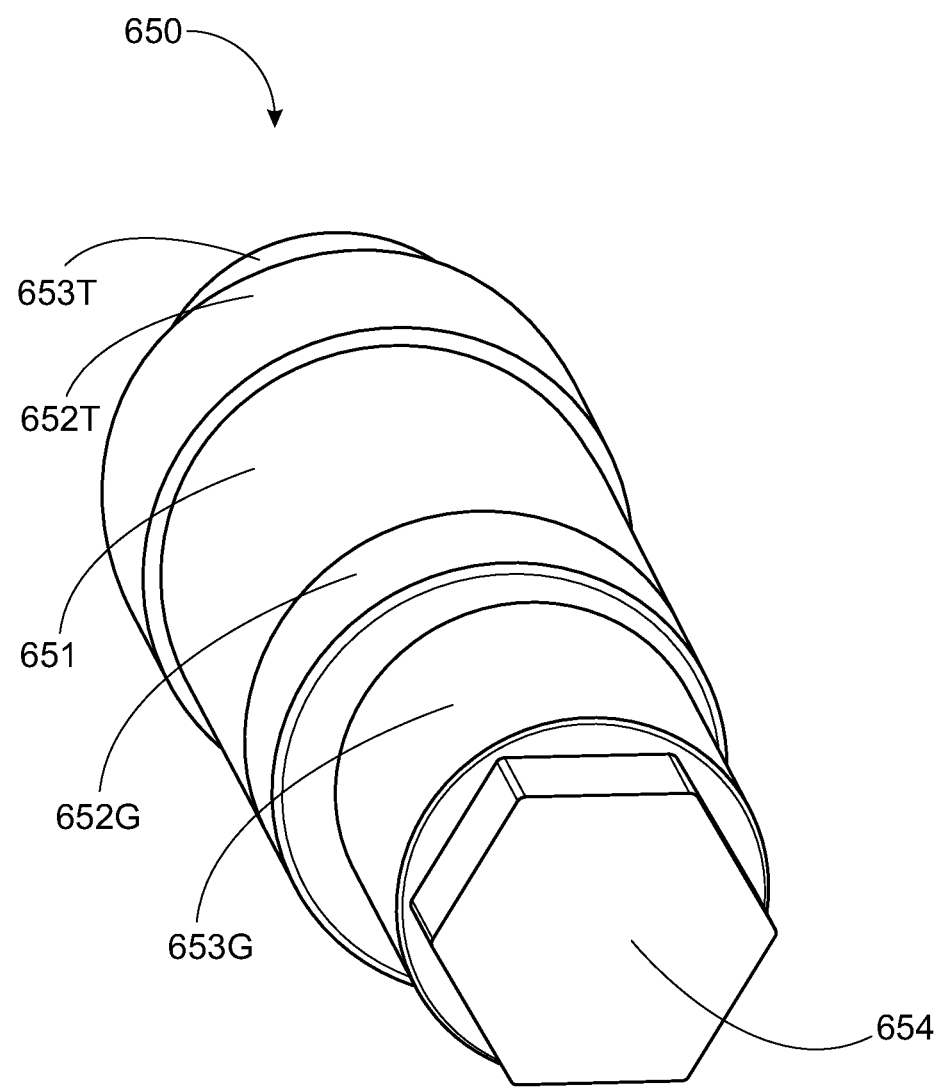
FIG. 6 depicts an axle comprising an eccentric section, suitable for use in the apparatus depicted in FIG. 4a, FIG. 4B and FIG. 5.
Figure 7:
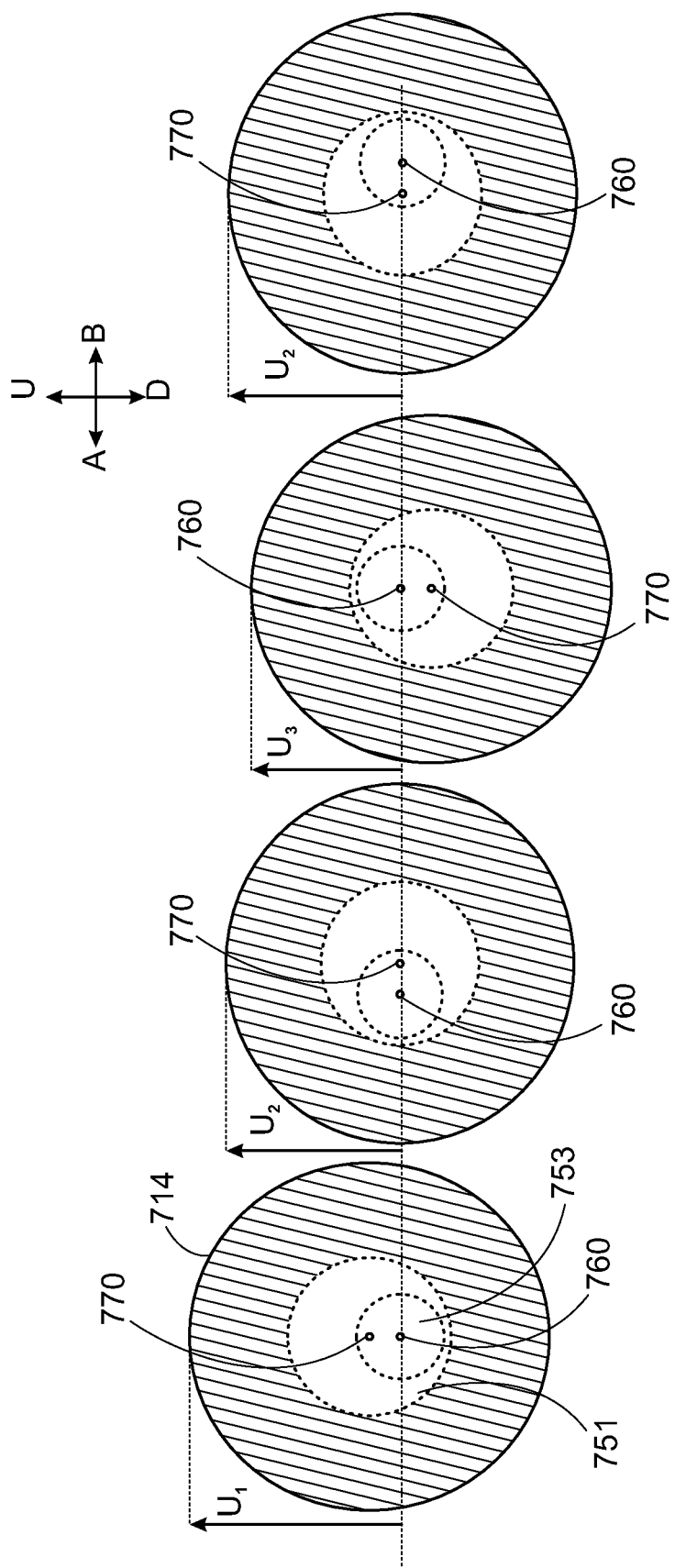
FIGS. 7a-d are schematic depictions of an axle suitable for use in the apparatus depicted in FIG. 4a, FIG. 4B and FIG. 5.

FIG. 6 depicts the axle 650 as described above in relation to FIGS. 4a, 4b, and 5. As noted above, the roller axle 650 is comprised of different sections along its length which have different radii. The axle 650 takes the form of an eccentric shaft, comprising an eccentric section position substantially centrally along the length of the shaft, and about which a roller will rotate in use.

The roller axle 650 includes the eccentric section 651 around which the roller will rotate in use, the clamping sections 652T,G, the holding sections 653T,G, and an axle cap 654. When positioned in the axle holder, the axle 650 is rotatable about an axle rotation axis defined by the central axis of the holding sections 653T,G. The holding sections 653T,G are configured to pass through the axle holder, and in particular to pass through the axle holding elements 632 of the axle holder, thereby defining the rotational axis for the axle 650.

As can be appreciated from the figures, the first section 651 is eccentric, i.e. offset, with respect to the holding sections 653T,G. Equivalently, the first section 651 is eccentric, i.e. offset, with respect to the axle rotation axis. As such, the rotational axis of the roller will also be offset from the axle rotational axis.

The first section 651 is not positioned centrally with respect to the axle rotational axis. In other words, the central axis of the first section 651 does not align with the axle 650 rotational axis. The first section 651 is substantially cylindrical, and its central axis may be parallel with the axle 650 axis of rotation. In use, the axle 650, each of its sections and the rotation axis of the axle 650 are positioned substantially parallel with the gantry rotation axis.

The clamping sections 652T,G are shown here, but are optional. These clamping sections 652T,G share a common central axis and are also offset with respect to the rotation axis of the axle 650, to the same degree and in the same manner as the first section 651.

The axle cap 654 is located at the G end of the axle 650. The axle cap 654 provides the means by which the axle 650 can be rotated around its rotational axis. The axle cap 654 may differ in radius from at least the second section 653G of the axle 650. The central axis of the axle cap 650 aligns with the axle 650 rotation axis. As such, the rotation of the axis 650 via the axle cap 654 rotates the axle 650 about its rotational axis.

The offset nature of the first section 651 of the axle 650 causes the first section 651 to be rotated about a point other than its geometrical centre. As the first rotatable roller rotates about first section 651 when in use, a rotation of the axle 650 causes a displacement of the rotatable roller in any radial direction relative to the axle 650 rotation axis. Thus, the axle 650 is configured such that, by rotating the axle 650 about the axle 650 rotation axis, the rotatable roller may be displaced in any radial direction relative to the axle rotation axis.

FIGS. 7a-d are schematics depicting a rear view of a roller 714 configured to rotate about an axle which comprises a first section 753 and a holding section 753. The optional clamping sections of the axle are not shown here for clarity. FIGS. 7a-d depict the same arrangement, with the axle having been rotated successively through 90°. In each of FIGS. 7a-d, the axle's centre of rotation 760 and the roller's centre of rotation 770 are depicted. As an example, the axle may be configured such that the distance between these axes of rotation is approximately 5 mm.

In FIG. 7a, the roller 714 is at its maximal displacement in the u direction. Arrow $U_1$ depicts the distance from the axle axis of rotation 760 to the outer circumference of the roller 714 in the U direction. FIG. 7b depicts the same roller 714 and axle, where the axle has been rotated about its axis of rotation 760. The roller 714 is now at its maximal displacement n the b direction. Arrow $U_2$ depicts the distance from the axle axis of rotation 760 to the outer circumference of the roller 714 in the u direction. It will be appreciated from inspection of FIG. 7b that rotation of the axle 90° about its rotation axis 760 has caused the roller 714 to move in the d and b directions, i.e. in a direction perpendicular with the radiotherapy axis of rotation. Accordingly, $U_1 > U_2$. The roller axis of rotation 770, located along the central axis of the first, central section of the axis 751, has also been displaced with respect to the axle axis of rotation, and in particular has been rotated in a clockwise direction with respect to the configuration depicted in FIG. 7a.

FIGS. 7c and 7d depict the roller 714 in its maximal displacement in the d and a directions respectively. $U_2 > U_3$. Because the first section 760 of the axis (around which the roller 714 rotates) is offset with respect to the section of the axis which defines the axle rotation axis 760, it can be appreciated that rotating the axle has the effect of rotating the roller axis of rotation 770 about the axle's axis of rotation 760. In other words, rotating the axle causes the roller to be displaced in a direction perpendicular to the axle rotation axis. Because the axle is positioned substantially parallel with the gantry rotation axis, the displacement direction is also substantially perpendicular to the gantry rotation axis. By rotating the axle about its rotation axis 760 in a first rotational direction (for example clockwise, as is depicted moving in order through FIGS. 7a-d), the first roller rotation axis 770 is also rotated in the first rotational direction.

The apparatus disclosed herein thus provides a means of mitigating the 'corkscrew effect' via repositioning or adjustment of one or more rotatable rollers which support the apparatus. By implementing the present disclosure, any of the rollers supporting the gantry can be made independently adjustable in space to provide adjustment of the gantry. By adjusting one or more of the rollers in the a,b,u,d directions, a sweet spot can be found in which the corkscrew effect is reduced or eliminated entirely. The adjustment is mechanically simple, meaning the adjustment means is unlikely to fail or require repair. The use of eccentrics in the manner described minimises the complexity of adjustment, maintains the axle axes on a horizontal plane, and provides the ability to correct any minor error in the gantry rotational axis (i.e. to bring it back into alignment with the horizontal).

Figure 8:
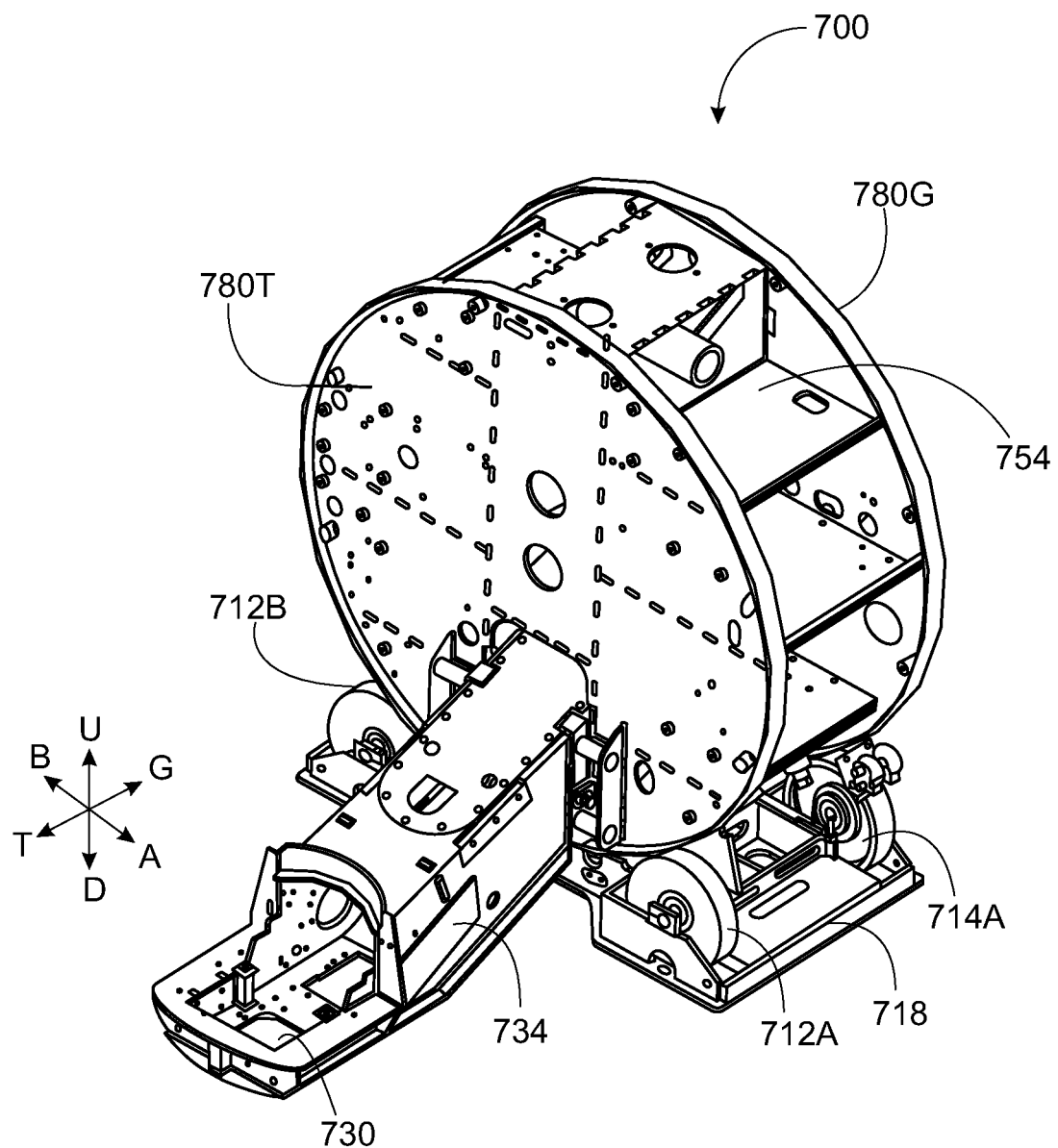
FIG. 8 depicts a radiotherapy apparatus in accordance with the present disclosure.

FIG. 8 depicts a radiotherapy apparatus 700 according to the present disclosure having a plurality of support wheels, including two stationary front wheels 712A and 712B and two adjustable rear wheels comprising an A-side rear wheel 714A and a B-side rear wheel 714B (not shown in the figure). A mechanical arm 534 extends from the gantry 754 toward housing 730. While not shown here, the housing 730 is configured to hold the radiation source and/or the beam generation system.

The front wheels 712A,B are configured to rotate about their respective axles, which are each held in place by respective axle holders on the under-gantry support structure 718. The front wheels 712A,B are displaced from one another along the A-B axis, and the rear wheels 712A,B are also displaced from one another along the A-B axis. The front wheels 712A, B are displaced from the rear wheels 714A,B along the T-G axis. Any single wheel or combination of the front or rear wheels may be drive wheels, however in this implementation each of the front and rear wheels is a drive wheel (drive means such as rotary motors not shown in the figure). The gantry further comprises two rims around its circumference, where the front wheels 712A,B support the gantry 754 via contact with the front rim 780T, and where the rear wheels 714A,B support the gantry 754 via contact with the rear rim 780G. By driving each of the wheels together, the angle of rotation of the gantry 754 (and hence the radiation source) can be controlled.

The rear wheels 714A,B are both adjustable via the means described above. In particular, the apparatus 700 comprises rear axles about which the rear wheels spin, and each rear axle is configured such that rotation of the axle about its rotation axis displaces its wheel in a direction substantially perpendicular to the T-G axis.

Accordingly, it will be appreciated that the apparatus 700 comprises a plurality of rollers 712A, 712B, 714A, and 714B (not shown in the figure). The apparatus comprises a first axle about which a first roller 714A rotates, and the first axle itself is configured to rotate about a first axle rotation axis. The first axle is configured such that rotation of the first axle about the first axle rotation axis displaces the first rotatable roller 714A in a direction substantially perpendicular to the gantry rotation axis, in the manner described above with respect to FIGS. 4a to 7d. A second rotatable roller 714B of the plurality of rotatable rollers is configured to rotate about a second roller axle. The second axle is configured such that rotation of the second axle about the second axle rotation axis displaces the second rotatable roller 714B in a direction substantially perpendicular to the gantry rotation axis, in the manner described above with respect to FIGS. 4a to 7d. The first and second axles are horizontally displaced, i.e. separated, with respect to each other along the A-B axis, i.e. along an axis substantially perpendicular to the gantry rotation axis. This displacement is achieved by virtue of the support structure 718 comprising a first axle holder configured to hold the first axle and a second axle holder configured to hold the second axle, where the first and second axle holders are displaced from one another along the A-B axis.

Upon installation of the apparatus 700, the drive wheels are driven in order to rotate the gantry 754, and the gantry is monitored for a corkscrewing movement in a direction along the T-G axis. If the gantry 754 is exhibiting signs of the corkscrewing effect, then one or both of the rear wheels may be adjusted. Rotation of the gantry can then be checked again for evidence of the corkscrewing effect. The process can be repeated until the effect has been sufficiently mitigated, or eliminated entirely.

Accordingly, disclosed herein is a method, which may be performed for example upon installation or during routine repair and servicing of a radiotherapy device. The method involves displacing a first roller of a plurality of rotatable rollers positioned underneath a gantry of a radiotherapy device. The radiotherapy device may be a radiotherapy device in accordance with any of the implementations disclosed herein, and comprises: rotating a first axle about its rotation axis to displace a first rotatable roller in a direction substantially perpendicular to the gantry rotation axis. The method may further comprise effecting a rotation of the gantry, monitoring for linear movement of the gantry in a direction substantially parallel with its rotation axis, and adjusting/displacing the first rotatable roller based on any detected motion during the monitoring. This may be an iterative process comprising several rounds of monitoring and adjustment until the corkscrew effect has been sufficiently mitigated.

Because both the rear wheels 714A,B may be displaced/moved/adjusted, the entire rear face of the gantry can be adjusted. For example, by displacing both rear wheels 714A,B in the A direction, the entire rear rim 718G and rear face of the gantry is moved in the A direction. This type of adjustment is the type of adjustment depicted in FIGS. 3a-d and described above. The advantage of this arrangement, i.e. translating the rear of the gantry in this way using two independently adjustable rollers, means that the corkscrew effect can be mitigated while the height of the gantry rotational axis can be kept reasonably constant throughout the adjustment, the gantry rotational axis is kept horizontal throughout the adjustment, and maintains the perpendicular relationship between the radiation beam and the gantry rotational axis. By providing an eccentric cam configuration on both the rear wheels, or equivalently on both the front wheels, they can be arranged in such a way that when both eccentrics are rotated to translate the gantry substantially in a lateral direction, one eccentric lifts the gantry slightly while the other eccentric lowers the gantry slightly. The resultant lateral shift in the height is negligible, meaning the horizontal axis remains substantially unmoved and horizontal. The corkscrewing effect can therefore be mitigated or eliminated, without changing the position of the isocenter and hence negatively impacting the accuracy of radiotherapy.

Adjusting both the rear wheels may result in a very small displacement of the x-ray source laterally. According to implementations of the present disclosure, this small displacement can be accommodated in two ways, for example by laterally adjusting or positioning the patient support system or a gantry support system to counter the displacement; or by adding a further adjustment to the other set of wheels (in this case front wheels) to move them in substantially the opposite direction. Thus, the adjustment at front and rear could be designed to give a zero lateral displacement but still displace the rear wheels laterally with respect to the front wheels and have the desired effect on minimizing or reducing corkscrewing.

It is to be understood that the above description is intended to be illustrative, and not restrictive. Many other implementations will be apparent to those of skill in the art upon reading and understanding the above description. Although the present disclosure has been described with reference to specific example implementations, it will be recognized that the disclosure is not limited to the implementations described, but can be practiced with modification and alteration within the spirit and scope of the appended claims. Accordingly, the specification and drawings are to be regarded in an illustrative sense rather than a restrictive sense. The scope of the disclosure should, therefore, be determined with reference to the appended claims, along with the full scope of equivalents to which such claims are entitled.

In this document, the terms "a" or "an" are used, as is common in patent documents, to include one or more than one, independent of any other instances or usages of "at least one" or "one or more." In this document, the term "or" is used to refer to a nonexclusive or, such that "A or B" includes "A but not B," "B but not A," and "A and B," unless otherwise indicated. In the appended claims, the terms "including" and "in which" are used as the plain-English equivalents of the respective terms "comprising" and "wherein." Also, in the following claims, the terms "including" and "comprising" are open-ended, that is, a system, device, article, or process that includes elements in addition to those listed after such a term in a claim are still deemed to fall within the scope of that claim. Moreover, in the following claims, the terms "first," "second," and "third," etc. are used merely as labels, and are not intended to impose numerical requirements on their objects.

What is claimed is:

1. A radiotherapy apparatus comprising:
a gantry rotatable about a gantry rotation axis; and
a plurality of rotatable rollers positioned underneath the gantry and configured to support the gantry, wherein a first rotatable roller of the plurality of rotatable rollers is configured to rotate about a first axle, wherein the first axle is configured to rotate about a first axle rotation axis, and wherein the first axle is configured such that rotation of the first axle about the first axle rotation axis displaces the first rotatable roller in a direction substantially perpendicular to the gantry rotation axis.

2. The radiotherapy apparatus of claim 1, further comprising:
a support structure comprising a first axle holder configured to support the first axle and define the first axle rotation axis.

3. The radiotherapy apparatus of claim 2, wherein the first axle comprises one or more different sections along its length, including an eccentric section positioned eccentrically with respect to the first axle rotation axis, the eccentric section having a different radius compared to other sections of the axle, and wherein the first rotatable roller is configured to rotate about the eccentric section.

4. The radiotherapy apparatus of claim 3, wherein the eccentric section is offset with respect to the first axle rotation axis.

5. The radiotherapy apparatus of claim 3, wherein the eccentric section has a central axis, wherein the central axis is parallel with, but does not align with, the first axle rotation axis.

6. The radiotherapy apparatus of claim 3, wherein the eccentric section defines a first roller rotation axis about which the first rotatable roller rotates, wherein the first roller rotation axis is displaced from the first axle rotation axis.

7. The radiotherapy apparatus of claim 6, wherein the first axle is configured such that, by rotating the first axle about the first axle rotation axis in a first rotational direction, the firs roller rotation axis is rotated in the first rotational direction.

8. The radiotherapy apparatus of claim 3, wherein the first axle further comprises:
two or more holding sections positioned on either side of the eccentric section, wherein the two or more holding sections pass through the first axle holder.

9. The radiotherapy apparatus of claim 8, wherein the two or more holding section are substantially cylindrical, and wherein the two or more holding sections have a shared central axis aligned with the first axle rotation axis.

10. The radiotherapy apparatus of claim 1, wherein the plurality of rotatable rollers comprises at least one drive roller configured to drive rotation of the gantry.

11. The radiotherapy apparatus of claim 1, wherein the plurality of rotatable rollers further comprises a second rotatable roller, wherein the second rotatable roller is configured to rotate about a second roller axle, wherein the second roller axle is configured to rotate about a second axle rotation axis, and wherein the second roller axle is configured such that rotation of the second roller axle about the second axle rotation axis displaces the second rotatable roller in a direction substantially perpendicular to the gantry rotation axis.

12. The radiotherapy apparatus of claim 11, wherein the first axle and the second roller axle are horizontally displaced with respect to each other along an axis substantially perpendicular to the gantry rotation axis.

13. The radiotherapy apparatus of claim 11, wherein the first rotatable roller and the second rotatable roller are both positioned either toward a rear of the gantry or toward a front of the gantry.

14. A method for displacing a first rotatable roller of a plurality of rotatable rollers positioned underneath a gantry of a radiotherapy device, wherein each roller in the plurality of rotatable rollers is configured to support the gantry, wherein the gantry is rotatable about a gantry rotation axis, wherein the first rotatable roller of the plurality of rotatable rollers is configured to rotate about a first axle, wherein the first axle is configured to rotate about a first axle rotation axis, and wherein the first axle is configured such that rotation of the first axle about the first axle rotation axis displaces the first rotatable roller in a direction substantially perpendicular to the gantry rotation axis, the method comprising:
rotating the first axle about the first axle rotation axis to displace the first rotatable roller in the direction substantially perpendicular to the gantry rotation axis.

15. The method of claim 14, wherein the first axle includes an eccentric section, wherein the eccentric section is positioned eccentrically with respect to the first axle rotation axis, and wherein the first rotatable roller rotates around the eccentric section.

16. A radiotherapy device comprising:
a gantry;
one or more rotatable rollers positioned underneath the gantry, wherein the gantry is rotatable about a gantry rotation axis, wherein the one or more rotatable rollers are configurable to support the gantry, wherein a first rotatable roller of the one or more rotatable rollers is configurable to rotate about a first axle, wherein the first axle is configurable to rotate about a first axle rotation axis, wherein the first axle rotation axis is configured such that rotation of the first axle about the first axle rotation axis displaces the first rotatable roller in a direction substantially parallel to the gantry rotation axis, and wherein a second rotatable roller is configurable to rotate about a second roller axle, wherein the second roller axle is configured to rotate about a second axle rotation axis, and wherein the second roller axle is configured such that rotation of the second roller axle about the second axle rotation axis displaces the second rotatable roller in a direction substantially perpendicular to the gantry rotation axis; and
a support structure, the support structure including a first axle holder configurable to support the first axle and define the first axle rotation axis.

17. The radiotherapy device of claim 16, wherein the first axle includes an eccentric section, wherein the eccentric section is positioned eccentrically with respect to the first axle of rotation, wherein the eccentric section is offset with respect to the first axle rotation axis, and wherein the first rotatable roller is configurable to rotate about the eccentric section.

18. The radiotherapy device of claim 17, wherein the eccentric section defines a first roller rotation axis about which the first rotatable roller rotates, wherein the first roller rotation axis is displaced from the first axle rotation axis, and wherein the first axle is configured such that, by rotating the first axle about the first axle rotation axis in a first rotational direction, the first roller rotation axis is rotated in the first rotational direction.

* * * * *